United States Patent [19]
Elseth

[11] Patent Number: 5,621,391
[45] Date of Patent: Apr. 15, 1997

[54] WOOD MOISTURE CONTENT MEASURING PROBE

[75] Inventor: Jeffrey J. Elseth, Grants Pass, Oreg.

[73] Assignee: Wagner Electronic Products Co., Inc., Rogue River, Oreg.

[21] Appl. No.: 389,923

[22] Filed: Feb. 15, 1995

[51] Int. Cl.$^6$ .................................................. G08B 21/00
[52] U.S. Cl. ........................... 340/604; 340/620; 324/689; 324/690; 73/866.5
[58] Field of Search ..................................... 340/604, 605, 340/620; 324/389, 690, 687; 73/866.5

[56] References Cited

U.S. PATENT DOCUMENTS

| | | | |
|---|---|---|---|
| 3,581,197 | 5/1971 | Morey, Jr. | 324/689 |
| 4,683,418 | 7/1987 | Wagner et al. | 324/689 |
| 5,023,560 | 6/1991 | Gallagher | 324/664 |
| 5,402,076 | 3/1995 | Havener et al. | 324/689 |
| 5,488,312 | 1/1996 | Havener et al. | 324/689 |

OTHER PUBLICATIONS

Model *L602 Hand Held Moisture Meter with Stack Probe* Brochure, Wagner Electronics, Inc., 1992.

*Primary Examiner*—Jeffery Hofsass
*Assistant Examiner*—Julie B. Lieu
*Attorney, Agent, or Firm*—Klarquist Sparkman Campbell Leigh & Whinston

[57] ABSTRACT

A probe for measuring the moisture content of wood in the center of a stack of wood has a moisture content sensor near a first or forward end thereof. The forward end of the probe is bendable and in one form is articulated. An extendable member also is mounted at the forward end of the probe. The extendable member is pivoted by a slide handle at an opposite end of the probe between reclined and extended positions. The forward end of the probe is inserted into a stack of wood between layers of the stack. The extendable member is extended to press the sensor against wood in the center of the stack. A meter connected to the sensor then registers the moisture content of the wood.

18 Claims, 5 Drawing Sheets

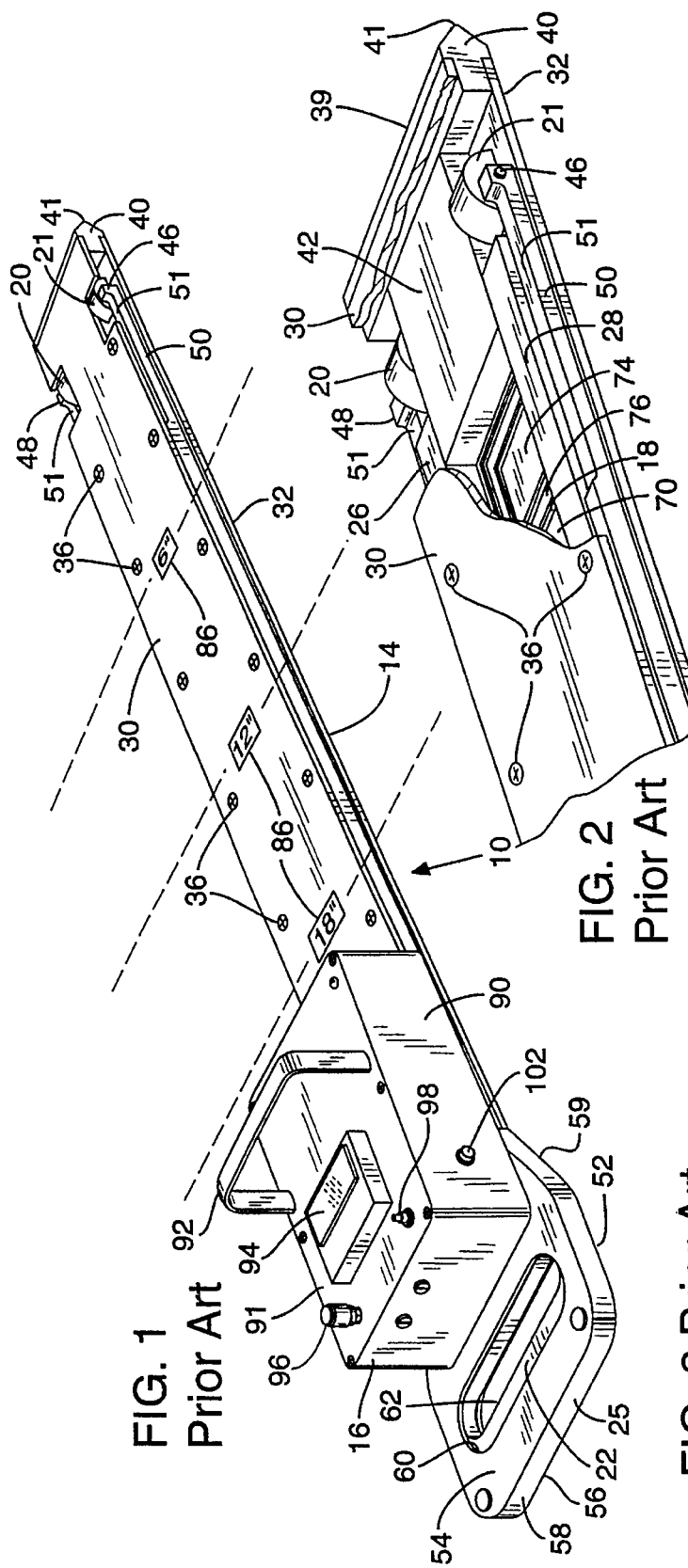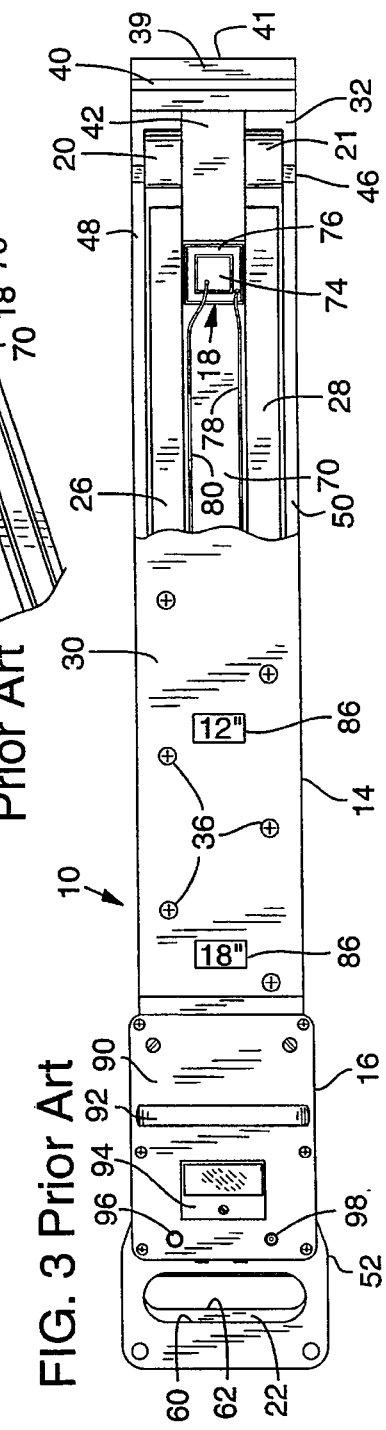

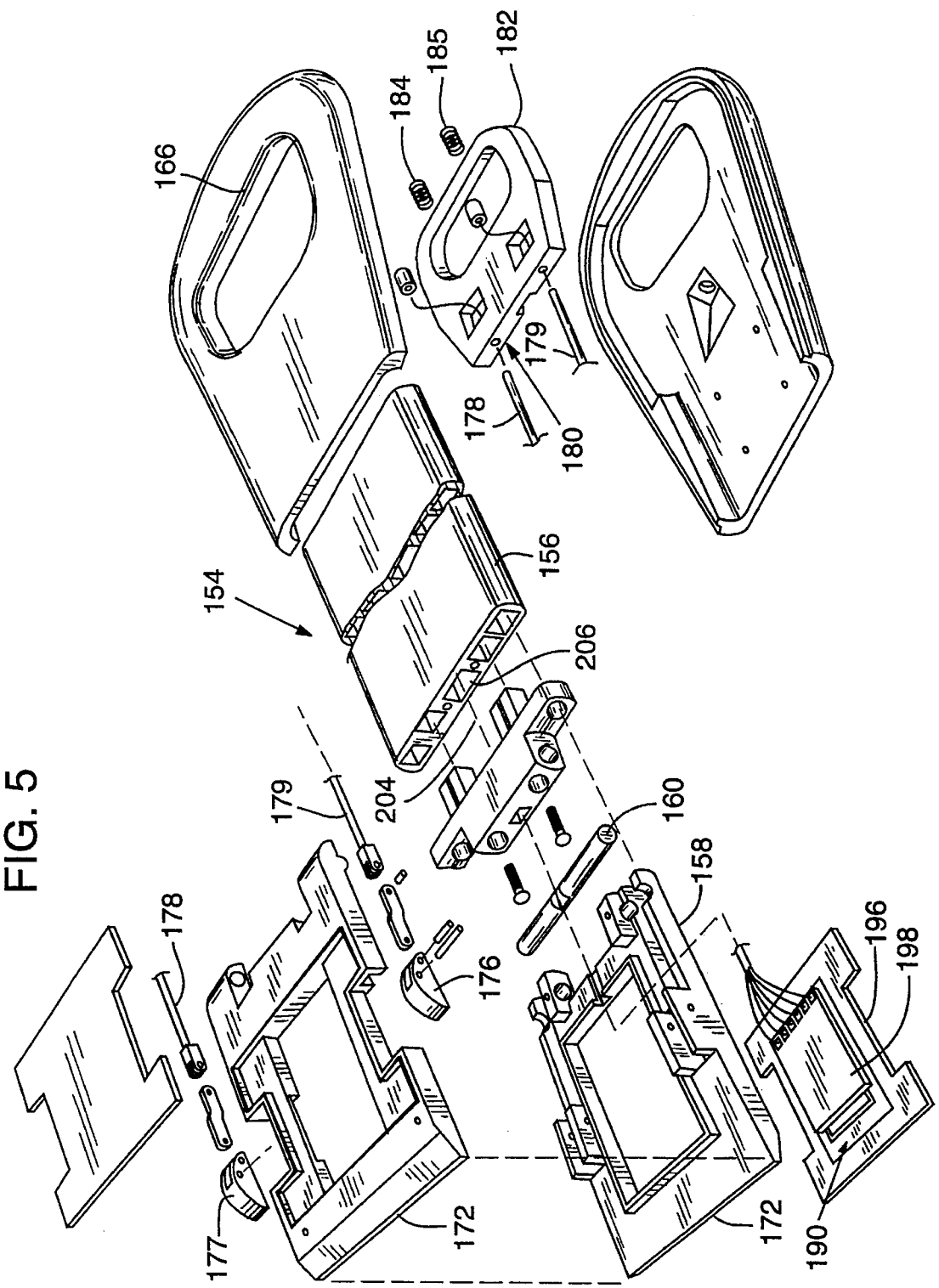

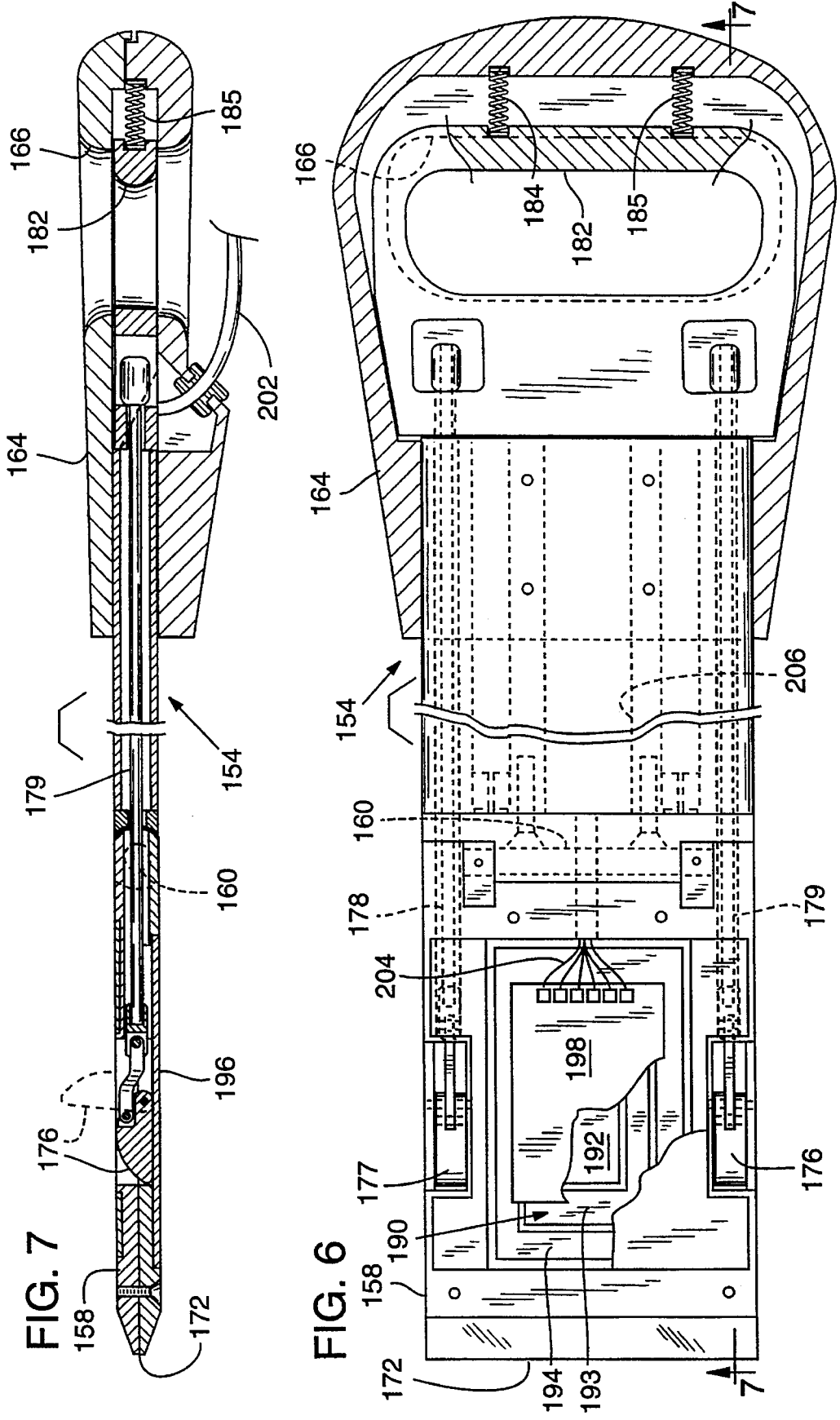

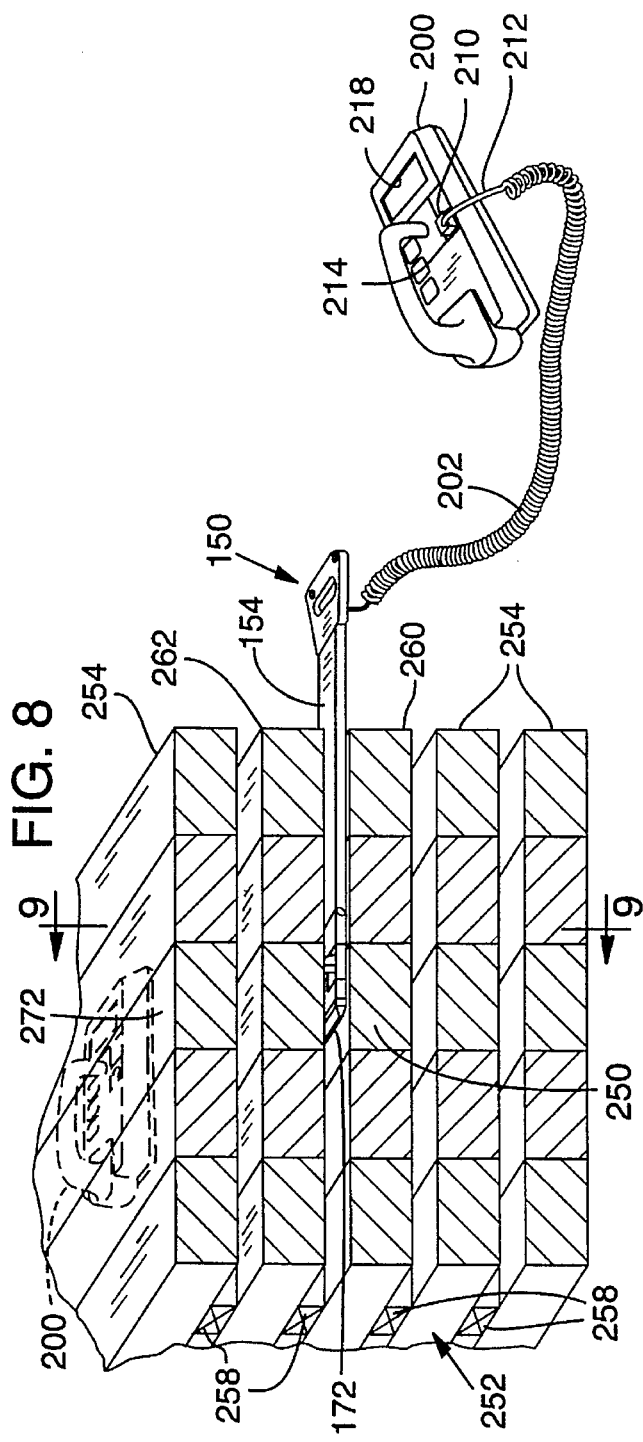
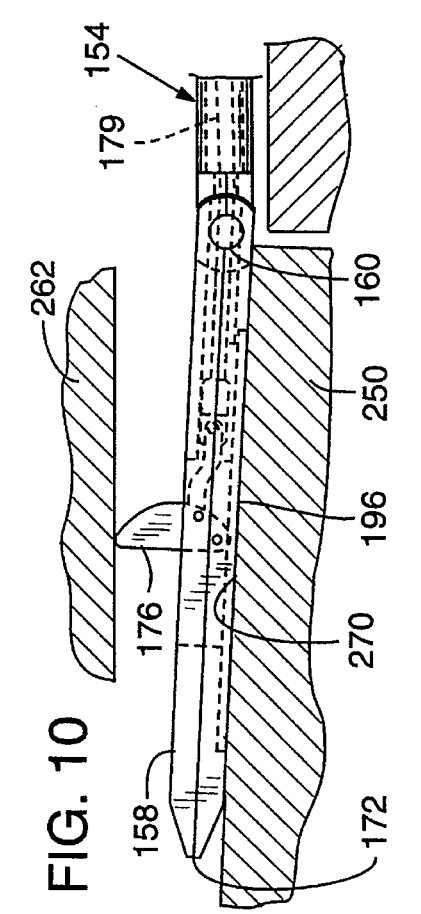
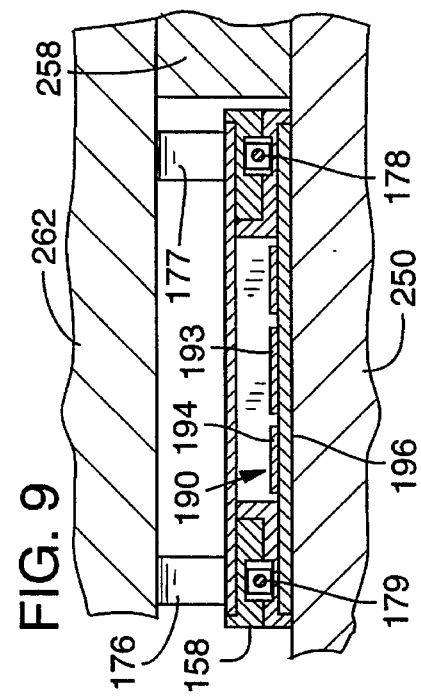

WOOD MOISTURE CONTENT MEASURING PROBE

FIELD OF THE INVENTION

The present invention relates generally to moisture detection devices and, more particularly, relates to a device for detecting the moisture content of wood using electromagnetic waves.

BACKGROUND OF THE INVENTION

After logs are milled to form lumber, the lumber is usually stacked for drying. Typically, the lumber is stacked in layers separated by transversely extending spacers called "stickers." For example, each layer of a stack may consist of two inch by four inch beams (two by fours) laid side by side lengthwise. Layers in a stack could also consist of beams of other dimensions, boards, planks, or the like. Between each layer, one inch by two inch or other dimensioned stickers are laid crosswise to the two by fours to allow air to circulate around and dry the two by fours. Often, the stacks are located in a kiln or drying oven to provide a controlled, heated environment for more rapid drying.

Usually, the lumber on the outer sides of a stack is subjected to a greater circulation of dry air than is the lumber in the stack's center, resulting in the lumber on the outer sides drying faster. Also, the lumber in the same layer of a stack may vary significantly in its initial moisture content. Therefore, estimating the dryness of the lumber in the stack's center by measuring the moisture content of the lumber on the outer sides of the stack is usually inaccurate. To better regulate the drying process, it is frequently desirable to determine the moisture content of the lumber in the center of a stack of wood without having to remove lumber from the stack.

One type of moisture detector used to measure the moisture content of wood uses two pin-shaped electrodes which are driven a predetermined distance apart into a piece of wood. With the electrodes inserted into a piece of wood, the moisture detector applies a voltage across the two electrodes and measures the current flowing between the electrodes. The amount of current flowing between the electrodes for a given voltage difference between the electrodes is directly related to the moisture content of the wood. Thus, by properly scaling the measured amount of current flow, the moisture detector is able to determine the moisture content of wood.

There are several problems with using this type of moisture detector to determine the moisture content of wood in the center of a stack of wood. First, it is difficult to drive pin-shaped electrodes into the wood in the stack's center. One apparatus which attempts to overcome this limitation comprises a rod with a T-shaped handle at one end. A flange is mounted at an end of the rod opposite the handle and projects perpendicularly to the rod. Two pin-shaped electrodes are mounted to project in the same direction perpendicularly from the flange approximately one and a half inches from the rod. The electrodes are connected to wires which run through a hollow center of the rod to a co-axial cable connector attached to the handle. A meter which provides a voltage to the electrodes and measures the current flow is connected to the electrodes by the co-axial cable connector.

The rod and flange act as a lever arm for driving the electrodes into a piece of wood in the center of a stack. First, the rod is inserted between layers of the stack with the flange oriented horizontally and the electrodes pointing upwards. With the electrodes pointing towards a piece of wood in the layer of the stack above the device, the rod is rotated about its longitudinal axis using the handle. During rotation, the rod seats against the layer of the stack beneath the apparatus and the flange rotates upward. This moves the electrodes on the flange toward the wood and drives them into the wood.

A second problem with moisture measurement devices employing pin-shaped electrodes is that because the electrodes are driven into the wood, the wood is damaged when its moisture content is measured. A further problem is that it is difficult to measure the moisture deep within a piece of wood. To measure the moisture deeply within the wood, considerable force must be used to drive the electrodes deeply into the wood, resulting in even greater damage to the wood.

A second type of device for measuring the moisture content of wood uses an electromagnetic wave detection technique. One such device is the prior art Hand-Held Moisture Meter Model L601 (the L601 Meter) manufactured by Wagner Electronic Products. The L601 meter has a sensor comprising three electrodes: a transmitting, a receiving, and a ground electrode. These electrodes are configured as flat conducting plates which are placed against or in close proximity to a piece of wood whose moisture content is to be measured.

The transmitting electrode is driven with a radio frequency (RF) excitation signal generated by an oscillator circuit to produce electromagnetic waves. When the electrodes are placed against or in close proximity to wood, the electromagnetic waves penetrate into the wood in a volume which is approximately 1 inch deep and 3 inches square. The electromagnetic waves induce an RF sensing signal in the receiving electrode whose amplitude is related to the moisture content of the wood. The L601 Meter displays the amplitude of the RF sensing signal on an analog display calibrated to show the moisture content of the wood.

The L601 Meter and like electromagnetic wave detection devices eliminate the need for driving pin-shaped electrodes into wood to measure its moisture content. However, such devices are only effective for measuring wood which is readily accessible to such a device, such as on the edge of a lumber stack. Consequently, moisture measurements by such a device may not accurately reflect the actual moisture content of lumber of the center of the stack.

A probe type device, designated the L602 stack probe, has been offered for sale by Wagner Electronic Products for more than one year. This device is highly satisfactory, but does have several drawbacks. With this type of a device, it can be difficult to position sensor closely adjacent to the wood to be measured, thus affecting the accuracy of the measurements. In addition, this device lacks flexibility in certain applications wherein it is desired to eliminate an elongated probe, yet still measure the moisture content of wood.

SUMMARY OF THE INVENTION

In accordance with the present invention, a device for detecting the moisture content of stacked wood using electromagnetic wave detection is provided. The device comprises an elongated probe having an electromagnetic wave sensor at a first or forward end of the probe, and a handle at a second end. The probe is adapted such that a meter can be electrically coupled to the sensor for displaying a measurement of the moisture content of wood.

The probe is thin to fit between layers of stacked wood. By inserting the probe, forward end first, between stack layers, the sensor may be placed in close proximity to a piece of wood deep within the stack whose moisture content is to be measured. The probe can be maneuvered to place the sensor in the correct position between the layers by hand using the handle. In its correct position, the sensor, or the portion of the probe containing the sensor, should be pressed against the wood. When the sensor is correctly positioned, the meter determines the moisture content of the wood using electromagnetic waves.

Because the layer of the stack containing the wood to be measured is uneven or for other reasons, it is at times difficult to properly position the sensor so that it is pressed against the wood. In accordance with a further aspect of the invention, to aid in properly positioning the sensor against the wood, the device may additionally comprise a wedging element which can be remotely actuated by the user to urge the sensor against the wood which is being evaluated for moisture content. To further aid in positioning the sensor, the probe may include an articulated forward tip. The articulated tip bends as the wedging element is actuated such that the sensor which is on one side of the tip can be laid flush against the layer to be measured.

In an illustrated preferred embodiment, the wedging element is an extendable member that is actuated by a mechanism at the handle end portion of the device. Preferably, the wedging element is located on a side of the probe opposite the sensor. For example, if the sensor is located on a bottom side of the probe, the wedging element is located on a top side of the probe.

In the utilization of the extendable member, the probe is inserted between layers of a stack of wood as described above. After inserting the probe between layers of a stack of wood with the sensor directly above the wood to be measured (assuming the configuration with the sensor on the bottom side of the probe), the extendable member is actuated. Actuation of the extendable member extends it upwards away from the top side of the probe. As it is extended, the extendable member pushes the probe away from the layer of the stack above the probe and towards the layer below the probe. The sensor is thereby pressed against the layer below the probe. By applying a force to position the sensor against the wood, the accuracy of the moisture content measurement is increased.

In a preferred embodiment of the invention, the stack probe has a cord or cable for attachment to a hand-held moisture meter. The hand-held moisture meter can be detached from the stack probe and operated independently to measure moisture content of unstacked wood with its own built-in sensor. The meter also can be attached to the probe with the cord for displaying moisture content of stacked wood measured using the probe's sensor.

Additional features and advantages of the invention will be made apparent from the following detailed description of a preferred embodiment which proceeds with reference to the accompanying drawings.

BRIEF DESCRIPTION OF THE DRAWINGS

FIG. 1 is a perspective view of a prior art device for measuring the moisture content of stacked wood in accordance with a first embodiment of the present invention;

FIG. 2 is a cut-away perspective view of a portion of the prior art device shown in FIG. 1;

FIG. 3 is a cut-away top view of the prior art device shown in FIG. 1;

FIG. 5 is an exploded perspective view of the stack probe shown in FIG. 4;

FIG. 6 is a top view, partly cut away, of the stack probe shown in FIG. 4; and

FIG. 7 is a cross-sectional side view of the stack probe shown in FIG. 4.

FIG. 8 is a side view of the device shown in FIG. 4 while in use measuring the moisture content of a piece of lumber within a stack of wood;

FIG. 9 is a sectional view of the device shown in FIG. 4 taken on line 9—9; and

FIG. 10 is a side view of a portion of the device shown in FIG. 4.

DETAILED DESCRIPTION OF THE PREFERRED EMBODIMENTS

Figure 4:
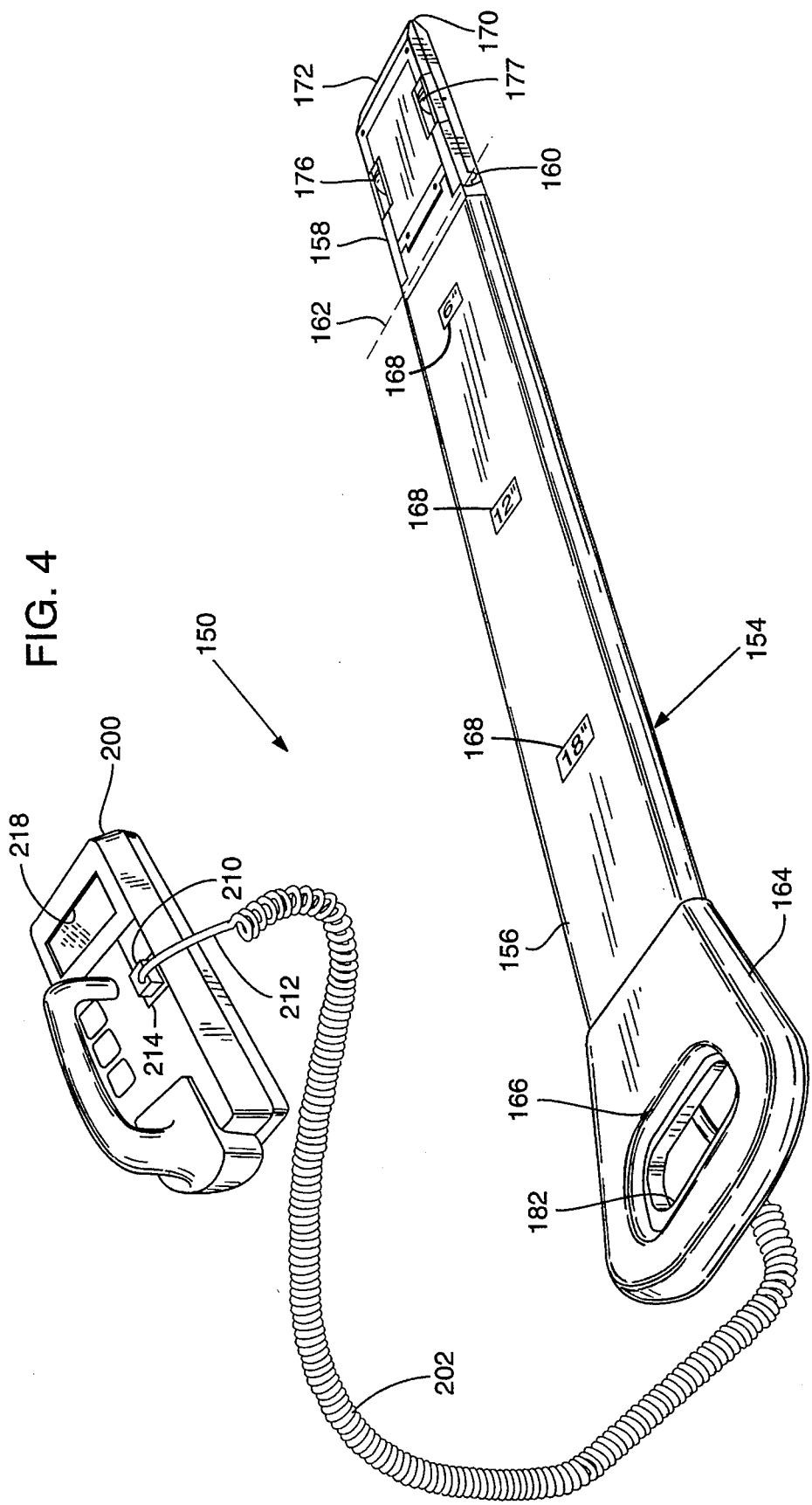
FIG. 4 is a perspective view of a device for measuring the moisture content of stacked wood having a stack probe and separate hand-held moisture meter in accordance with a second embodiment of the invention.

With reference to FIG. 1, a device 10 for measuring the moisture content of wood according to the prior art comprises a probe 14, a moisture content meter 16, an electromagnetic wave sensor 18 (shown in FIGS. 2 and 3), left and right cam levers 20, 21, and a slide handle 22. The probe 14 is a flattened, elongated member with the approximate dimensions of 34 ½ inches long by 5⅛ inches wide by ½ inch in height. The probe is thin enough to fit between layers of lumber separated by stickers. The sensor 18 is located within the probe near a bottom surface of the probe and approximately 4 inches from a forward end 24 of the probe. The cam levers 20, 21 are located on a top side of the probe, between the sensor 18 and the forward end 24 of the probe. The meter 16 is mounted on the top side of the probe at an opposite end 25 of the probe. The slide handle 22 is also at the opposite end 25 of the probe.

As shown in FIGS. 2 and 3, the probe 14 comprises left and right longitudinal support members 26, 28, and top and bottom cover plates 30, 32. The support members 26, 28 are parallel to each other and separated by a distance of approximately 2 inches. The support members 26, 28 are sandwiched between the cover plates 30, 32. The support members 26, 28 and the cover plates 30, 32 define a longitudinal hollow cavity between the support members 26, 28. The hollow cavity begins at the opposite end 25 of the probe beneath the meter 16 and extends nearly to the forward end 24 of the probe. Each of the cover plates 30, 32 is constructed of fiberglass or other suitable material. One specific material is a fiberglass circuit board material with an underlying copper sheet for shielding purposes, with the copper sheet being etched or otherwise separated to form RF electrodes 74, 76 for use as explained below. The cover plates 30, 32 are attached to the support members 26, 28 with screws 36. The heads of the screws 36 are flush with the outer surface of the cover plates 30, 32.

At the forward end 24, the probe 14 comprises a nose member 40 having a forward face 39 which tapers outwardly from the top and bottom to form a forward-projecting horizontal ridge 41 at the center of the forward face. The resulting wedge shape of the nose member 40 aids in guiding the insertion of the probe between the layers of lumber. The nose member 40 is attached to a forward end of a support block 42 which is approximately 2 inches in width. An opposite end of the support block fits between the support members 26, 28 at a forward extent of the hollow cavity in the probe 14. The nose member 40, support block 42, and support members 26, 28 are typically attached together, as with glue. Like the support members 26, 28, the nose member 40 and support block 42 are also sandwiched between the top and bottom cover plates.

The cam levers 20, 21 operate as extendable members for pressing the sensor against wood deep within a stack of wood. The cam levers 20, 21 are located between the support members 26, 28 and the nose member 40, one on each side of the support block 42. top cover plate 30 is notched or indented at this location so that the cam levers 20, 21 remain uncovered, allowing the cam levers 20, 21 to be extended above the probe 14.

Each of the cam levers 20, 21 have a planar bottom surface and a curved top surface. The cam levers 20, 21 are pivotally mounted at a rearward end on a pin 43 (FIG. 6) which extends through the support block 42. The cam levers 20, 21 pivot on the pin between a reclined position in which their bottom surfaces are flush (see FIG. 2) against the bottom cover plate 32 and an extended position in which their bottom surfaces are vertical (see FIG. 6). When in the reclined position, the curved top surfaces of the cam levers 20, 21 are flush with the top cover plate 30. In their extended position, however, the cam levers 20, 21 project outwardly from the probe and above the top cover plate 30.

The cam levers 20, 21 are also rotatably attached by pins 46 extending from a top center position on the outer sides of the cam levers to left and right arms 48, 50. The arms 48, 50 are slidable and extend along the left and right sides of the probe between the cover plates 30, 32 and next to the support members 26, 28. The arms 48, 50 are an extension of the slide handle 22 at the opposite end 25 of the probe 14. When the arms 48, 50 are moved towards the opposite end 25 of the probe by sliding the slide handle 22, the cam levers 20, 21 are moved from their reclined to their extended position. The arms 48, 50 have recessed portions 51 on their top sides near their forward ends to prevent the arms from rubbing or binding against the top cover plate 30 and restricting the pivoting motion of the cam levers 20, 21 as the arms 48, 50 are slid to actuate the cam levers.

Referring now to FIGS. 1 and 3, at the opposite end 25 of the probe 14, a casing 52 for the slide handle 22 is attached to the probe. The casing 52 comprises a top 54, a bottom 56, and a side wall 58 which define a hollow cavity in which the slide handle 22 is encased. The top and bottom walls 54, 56 of the casing 52 are level with the top and bottom cover plates 30, 32 respectively. Thus, the casing 52 has the same height as the probe 14. However, the casing 52 is wider than the probe 14 and tapers at a forward end 59 where it attaches to the probe.

An oblong opening 60 is provided in the top and bottom walls 54, 56 transverse to the longitudinal axis of the probe 14 and approximately one inch from the opposite end 25 of the probe. The opening 60 is sized to permit insertion of a hand into the opening. Within the hollow of the casing 52 is the slide handle 22. The slide handle 22 is a solid member which fits snugly but slidingly within the casing. A second oblong opening 62 through the slide handle is provided and aligns with the opening 60 in the casing 52. The opening 62 is narrower in width than the opening 60. This permits a user to slide the slide handle 22 between a forward position in which the forward sides of the openings 60, 62 are aligned and a rearward position in which the rearward sides of the openings 60, 62 are aligned. Further, when the slide handle is slid to the forward position, the arms 48, 50 are pushed forwardly placing the cam levers 20, 21 in their reclined position. When the slide handle is slid towards its rearward position, the arms are retracted rearwardly moving the cam levers 20, 21 to their extended position.

With reference to FIGS. 2 and 3, the sensor 18 is provided on the bottom cover plate 32 within the hollow cavity of the probe. The sensor 18 is formed from a portion of a conductive surface, such as copper, at an inside surface 70 of the bottom cover plate. More specifically, electrodes are formed by etching the copper on the inside surface 70. In the probe 14, the electrodes comprise an inner square copper electrode 74 and an outer square annular electrode 76 surrounding and spaced from the inner electrode 74. The electrodes are connected to the meter 16 with wires 78, 80. The copper-plated inside surface 70 is also connected to a ground wire of the meter 16. The electrodes 74, 76 are driven by the meter 16 with an RF excitation signal to produce electromagnetic waves. An RF sensing signal will be induced in the electrodes 74, 76 dependent on the proximity of the electrodes to wood and on the moisture content of the wood.

Referring again to FIG. 1, the probe 14 also comprises depth indicia 86 on an outer exposed surface of the probe, such as on the exposed surface of the top cover plate 30. The depth indicia 86 indicates the longitudinal distance along the probe from the center of the sensor 18 and may be used to determine how far the sensor has been inserted into a stack of wood. On the probe 14, the indicia consist of numerical labels placed at six inch intervals (namely, 6", 12" and 18").

Referring now to FIGS. 1 and 3, the meter 16 mounted on the top side of the probe comprises a box-shaped meter housing 90 having a lid 91 attached with screws. The housing 90 encases a rechargeable battery and circuitry for moisture detection using electromagnetic waves. To aid in handling the device 10, a U-shaped handle 92 is mounted transverse to the longitudinal axis of the probe on the lid 91. An analog needle and dial indicator 94 is also mounted on the lid 91. The indicator 94 has a scale which reads moisture content between 6 and 30 percent. The indicator 94 has a built-in electric bulb for illuminating the indicator when the device is used in dim light.

Also mounted on the lid 91 of the meter housing 90 are a calibration knob 96 and an actuation button 98. The actuation button turns on the meter 16 by providing power from the rechargeable battery to the circuitry encased in the housing. The circuitry includes an automatic shut-off feature to prevent unnecessary use of battery power. Thus, a needle in the indicator 94 registers the moisture content as measured by the sensor 18 after the actuation knob 98 is pressed. The calibration knob 96 is used to recalibrate the meter 16 to compensate for battery drain and other variable conditions. A zero-adjust screw (not shown) used to zero the meter 16 is located inside the housing 90. The zero-adjust screw may be accessed through a hole (not shown) in a side of the housing 90. The hole is normally covered with a dust cap.

The rechargeable battery in the meter housing 90 can be recharged with a conventional charging unit which plugs into a 110 Volt, 60 Hz AC power outlet. A charging socket 102 is provided in a sidewall of the housing 90 for this purpose. The charging socket 102 receives a standard connector provided on conventional charging units. One suitable meter 16 with the above described features is an L601 meter from Wagner Electronic Products of Rogue River, Oreg. Alternatively, other RF signal generating/receiving and indicating devices may also be used as meter 16.

With reference to FIGS. 4–7, a device 150 for measuring the moisture content of stacked wood according to a preferred embodiment of the invention comprises a probe 154 which is a flattened, elongated member having dimensions similar to that of the probe 14 of the device 10 (FIGS. 1–3). The probe 154 comprises a shaft portion 156 and an articulated tip 158 which are attached together at a joint or hinge 160. The joint 160 allows the articulated tip 158 to pivot about an axis 162 (FIG. 4) lateral to the probe 154. A moisture sensor 190 (described more fully below) is located in the articulated tip 158.

The shaft portion 156 widens at one end 164 opposite the joint 160. An oblong opening 166 at the widened end is sized for a hand, and serves as a handle for grasping the probe 154. Indicia 168 (FIG. 14) may be marked at intervals along the length of the probe 154 for indicating the depth of insertion of the probe's sensor 190 into stacked wood.

Top and bottom surfaces of the articulated tip 158 taper at a forward end 170 opposite the joint 160 to a horizontal forward edge or ridge 172. The tapered forward end 170 acts as a wedge to aid insertion of the probe between layers of stacked wood. Left and right cam levers 176–177 are pivotally mounted in the articulated tip 158 to move between reclined and extended positions. The cam levers 176–177 are attached to forward ends of a pair of parallel rod arms 178–179 (FIGS. 5–7) of a sliding handle actuator 180. The rod arms 178–179 are enclosed within the shaft portion 156. The rod arms 178–179 are attached at their opposite ends to a trigger portion 182 (FIGS. 5–7) of the sliding handle actuator 180. The trigger portion 182 is enclosed within the widened end 164 of the handle member 156 and accessible through the oblong opening 166 of the probe's shaft portion 156. The trigger portion 182 is slidable between a front position in which the cam levers 176–177 are in their reclined position and a rear position in which the cam levers are in their extended position. The trigger 182 is urged forwardly towards its front position by a pair of springs 184–185 (FIGS. 5–7), but can be manually pulled rearwardly to move the cam levers 176–177 from their reclined to their extended positions. When the trigger 182 is thereafter released, the springs 184–185 again return the cam levers 176–177 to their reclined position.

The moisture content sensor 190 (FIGS. 5 and 6) is enclosed within the articulated tip 158. The sensor 190 preferably comprises electrodes 192–194 etched onto an inner surface of a bottom plate 196 (FIG. 7) of the articulated tip 158, and configured similarly to the electrodes of the electromagnetic wave sensor 18 (FIG. 3) of the device 10. When driven with an alternating current signal, the electrodes 192–194 produce radio frequency electromagnetic waves within a space approximately 3 inches square and 1 inch deep beneath the sensor 190 in the articulated tip 158. The moisture content of wood within this space affects the driving signal so that the signal relates to the moisture content of wood within that space.

To avoid signal reflections associated with transmitting an alternating current signal on a long cable, a sensor driving electronic circuit preferably is provided on a printed circuit board 196 mounted over the sensor 190 in the articulated tip 158. When the articulated tip 158 is fully assembled, the printed circuit board 196 is fully enclosed within the articulated tip 158. The sensor driving circuit generates the alternating current, radio frequency signal which drives the sensor 190. The circuit additionally forms a direct current signal related to the moisture content of wood in proximity to the sensor. Suitable sensor driving electronic circuits are known, such as those used in the prior art Hand-Held Moisture Meter Model L601 and the Stack Probe Model L602 manufactured by Wagner Electronic Products, and may be for used in the invention.

The device 150 further comprises a moisture content meter 200 (FIG. 4) which preferably is a hand held moisture meter having its own built-in sensor and sensor driving electronic circuit (not shown) which can be operated independently of the probe 154, such as for moisture measurement applications (e.g. unstacked wood) in which the hand held meter can be directly positioned against the wood whose moisture content is to be measured. The meter's built-in sensor preferably is configured similarly to the probe sensor 190 and operates in the same fashion. A suitable hand-held moisture content meter 200 is the L612 Digital Recording Moisture Meter available from Wagner Electronic Products of Rogue River, Oreg.

For connection to the meter 200, the probe 154 has a multiple conductor cable 202 (FIGS. 4 and 7) attached at the widened end 164 of the handle member 156. The cable 202 is electrically coupled to the electronic circuit on the printed circuit board 196 with wires 204 (FIGS. 5 and 6) enclosed within a longitudinal hollow 206 (FIGS. 5 and 6) within the probe. A connector 210 (FIG. 4) at a free end 212 of the cable 202 is configured to mate with the connector 214 (FIG. 4) of the meter 200. When the cable connector 210 and meter connector 214 are mated, the meter 200 is electrically coupled to the sensor driving circuit on circuit board 196, and can read the moisture related signal it produces. The meter connector 214 includes a switch (not shown) which is actuated when the connector 210 is inserted into the connector 214 and operates to disable the meter's built-in sensor. Accordingly, when the meter 200 and probe 154 are connected, the meter 200 operates to display the moisture content of wood positioned in proximity to the sensor 190 of the probe 154. When the meter 200 is disconnected from the probe 154, the meter 200 operates independently to measure the moisture content of wood in proximity to its built-in sensor. Accordingly, the device 150 provides a meter 200 which can be operated independently or in conjunction with the probe 154. The measured moisture content is indicated on an LCD display 218.

FIGS. 8–10 illustrate the device 150 being used to measure the moisture content of a piece of wood ("target piece") 250 in a stack 252. The stack of wood 252 comprises a plurality of layers 254 of two by four beams laid side by side lengthwise. The layers 254 are separated by one inch by two inch stickers 258 which gaps of about ¾ to one inch in height between the layers.

Before the measurement is made, the meter 200 is connected to the probe 154, and suitably calibrated and/or zeroed. To measure the moisture content of the target piece 250, the probe 154 is inserted tapered forward edge 172 first between a layer 260 containing the target piece 250 and a layer 262 above it. The probe 154 is inserted into the stack 252 until the sensor 190 in the articulated tip 158 is over the target piece 250. The depth indicia 168 are used to judge the distance the probe 154 is inserted into the stack 252.

Once the sensor 190 is positioned over the target piece 250, the cam levers 176–177 are extended by pulling the trigger portion 182 of the sliding handle actuator 180 rearwardly. This causes the cam levers 176–177 to pivot upwardly toward the layer 262 above the target piece 250. As the cam levers 176–177 continue to pivot upwardly, they force the articulated tip 158 away from the layer 262 and against the target piece 250. Consequently, the sensor 190 is positioned closer to the piece of wood 250 for a more accurate measurement of the wood's moisture content.

The joint 160 in the probe 154 further facilitates the positioning of the sensor 190. For a more accurate moisture content measurement, the sensor 190 is ideally laid flush against the piece of wood 250 being measured. With the prior art device 10 which employed a probe 14 having a rigid configuration, a difficulty was sometimes encountered in positioning the sensor 18 flush against the target piece 250 in situations where the target piece presents a surface cannot be aligned parallel to the probe 14 (such as when the pieces of wood in the layer 260 are stacked unevenly or otherwise have unaligned top surfaces). In these situations, the rigid configuration of the probe 14 could prevent the sensor 18 from being positioned flush against the target piece 250.

With reference to FIG. 10, with the device 150 according to the invention, the sensor 190 in the articulated tip 158 can be positioned flush against a surface 270 of the target piece even when the surface can not be aligned parallel to the shaft portion 156 of the probe 154. With the probe 154 inserted into the stack 252 with the sensor 190 above the target piece as described above, the cam levers 176–177 are moved towards their extended positions by pulling the trigger portion 182 of the sliding handle actuator 180. This urges the sensor 190 in the articulated tip 158 towards the target piece. The probe 154 also bends at the joint 160 to permit the bottom plate 196 of the articulated tip 158 to be positioned flush against the target piece 250. The sensor can be suitably positioned thereby for a more accurate moisture content measurement.

After positioning the sensor 190, the user activates the meter 200. Whereupon, the moisture content percentage of the piece of wood 250 is indicated on the LCD display 218.

Referring to FIG. 8, when disconnected from the probe 154, the meter 200 is operable to measure the moisture content of wood independently from probe 154. Disconnecting the cable connector 210 from the meter connector 214 activates the switch in the meter connector that enables the meter's built-in sensor (not shown). Moisture content measurements can then be made by placing a bottom surface of the meter (the built-in sensor is located near the meter's bottom surface) against a surface of the wood to be measured, and activating the meter. The meter can be used in this manner to measure the moisture content of a piece of wood in an outer layer of the stack 252 as illustrated in FIG. 8, or of unstacked wood.

Having described and illustrated the principles of my invention with relation to a preferred embodiment, it will be recognized that the invention can be modified in arrangement and detail without departing from such principles. For example, various mechanical and fluid actuated mechanisms can be employed to urge the sensor at the end of the probe against the lumber to be tested. Therefore, the invention is not limited to the mechanical mechanism in the specifically described embodiment. To illustrate the breadth of this aspect of the invention, other exemplary mechanisms include the following.

A first exemplary mechanism is one that is gas or fluid operated. In such a mechanism, a balloon-like inflatable bag at the forward end of the probe is expanded to urge the sensor against lumber in a stack. The bag is expanded by operating a handle to push against a diaphragm at the opposite end of the probe. When pushed against using the handle, the diaphragm forces gas or fluid through a tube to fill the bag.

Another exemplary mechanism employs a push or twist rod linkage mechanism operated by a handle. When the rod is operated by a handle, the linkage mechanism forces a lever or the like to protrude outwardly from the forward end of the probe, urging the sensor in the against the lumber. A further exemplary mechanism employs a cable linkage similar to those used in bicycle brake systems. Such cable linkages can be employed to extend a lever at the forward end of the probe when operated by pulling a lever at the opposite end of the probe.

Also exemplary of the various mechanisms that can be employed to implement the invention are the various configurations available for an extendable member. For example, the extendable member can be configured as a single-piece cam lever rather than the separate cam levers 20, 21 of the preferred embodiment. Such a single-piece cam lever may comprise a bridge portion which straddles the support block 42 and cam portions shaped similarly to the cams 20, 21. Like the cam levers 20, 21, the single-piece cam lever may be pivotally mounted to the support block 42 and the arms 48, 50 to pivot between a reclined and an extended position. The cam levers 20, 21 of the device 10 are preferred over a single-piece cam lever of this type because the cam levers 20, 21 exhibit a reduced tendency to clog from trapped debris such as pitch and sawdust. Still other configurations of extendable members for the probe 14 are suitable to the present invention. Any wood surface engaging element capable of selective projection from the probe to urge the probe against the lumber being tested may be used.

Further, while the preferred embodiments of the invention have been illustrated as utilizing a radio frequency sensor (e.g. sensor 18 shown in FIG. 2), the invention is not limited to sensors of this type. The invention also can be beneficially applied to the positioning of any of various types of moisture sensors in the proximity of a layer in stacked wood whose moisture content is being measured. Accordingly, various other types of moisture sensors can be employed in alternative embodiments of the invention. More specifically, other types of sensors employing electromagnetic waves to sense moisture content in wood can be utilized, including particularly those sensors employing propagating electromagnetic waves in the microwave frequencies. These microwave sensors, however, are more costly than the illustrated radio frequency sensor. The illustrated radio frequency sensor therefore is preferred.

Accordingly, I claim as my invention all embodiments which come within the scope and spirit of the following claims and equivalents thereto.

I claim:

1. An apparatus for measuring the moisture content of stacked wood comprising:

an elongated probe having a first end portion, a second end portion, and a bendable portion between the first and second end portions, and supporting an electromagnetic wave responsive moisture sensor adjacent the first end portion;

a meter adapted to be electrically coupled to the probe sensor for displaying signals representing the moisture content of wood in proximity to the probe sensor; and the probe bending at the bendable portion while the first and second end portions remain straight when the second end portion is presented at an angle to the wood so as to urge the probe sensor toward the wood in proximity to the probe sensor.

2. An apparatus according to claim 1 in which the first end portion of the probe comprises an articulated tip of the probe.

3. An apparatus according to claim 2 comprising:

a wood surface engaging element located on the first end portion and selectively movable from a first position toward a second position projecting outwardly from the probe a greater distance than when in the first position, whereby with the probe inserted between a first and a second layer of stacked wood, movement of the engaging element toward the second position pushes the forward end of the probe away from the first layer and towards the second layer to place the probe sensor in closer proximity to the second layer.

4. An apparatus according to claim 3 comprising an actuator for moving the wood surface engaging element between the first and second positions.

5. An apparatus according to claim 2 in which the second end portion has a handle, the first and second end portions being connected by a joint, the articulated tip pivoting about the joint.

6. An apparatus according to claim 5 in which the first and second end portions have aligned holes, the joint comprising a pin engaged through the aligned holes.

7. An apparatus according to claim 5 comprising:

an extendable member located on the articulated tip and selectively movable between a reclined and an extended position, the extendable member when in the extended position projecting outwardly from the probe a greater distance than when in the reclined position, whereby with the probe inserted between a first and a second layer of stacked wood, movement of the extendable member toward the extended position pushes the forward end of the probe away from the first layer and towards the second layer to place the probe sensor in closer proximity to the second layer.

8. An apparatus according to claim 5 comprising:

an actuator for moving the extendable member between the reclined and extended positions.

9. An apparatus according to claim 8 wherein the actuator comprises a sliding handle member having a handle portion located at the second end portion of the probe and an arm portion extending longitudinally along the probe to the forward end of the probe, the arm portion engaging the extendable member at the articulated tip of the probe, the sliding handle member being slidable between a first and a second position to move the extendable member between the first and second positions, respectively.

10. An apparatus according to claim 1 in which the meter comprises a portable meter which is separable from the probe and is operable independently of the probe for measuring and indicating the moisture content of the wood.

11. An apparatus according to claim 10 in which the meter comprises an electromagnetic wave responsive moisture sensor for measuring the moisture content of wood independently of the probe sensor.

12. An apparatus according to claim 11 in which the meter comprises a connector for electrically coupling the meter to the probe sensor, the connector comprising means for disabling independent measurement of moisture content by the meter sensor.

13. The apparatus of claim 12 comprising:

a sensor driving circuit at the first end portion for driving the probe sensor with an alternating current signal.

14. An apparatus for measuring the moisture content of stacked wood comprising:

an elongated probe supporting an electromagnetic wave responsive moisture sensor adjacent a first end portion said probe bending at a bendable portion between the first end portion and the second end portion when the second end portion is presented at an angle to the wood while the first and second end portions remain straight;

a portable meter adapted to be electrically coupled to the probe sensor for displaying signals representing the moisture content of wood in proximity to the probe sensor, the meter being separable from the probe and operable independently of the probe for measuring and indicating the moisture content of the wood; and a wood surface engaging element located on the first end portion and selectively movable from a first position toward a second position projecting outwardly from the probe a greater distance than when in the first position, whereby with the probe inserted between a first and a second layer of stacked wood, movement of the engaging element toward the second position pushes the forward end of the probe away from the first layer and towards the second layer.

15. An apparatus according to claim 14 comprising an actuator for moving the wood surface engaging element between the first and second positions.

16. An apparatus according to claim 14 in which the meter comprises an electromagnetic wave responsive moisture sensor for measuring the moisture content of wood independently of the probe sensor.

17. An apparatus according to claim 16 in which the meter comprises a connector for electrically coupling the meter to the probe sensor, the connector comprising means for disabling independent measurement of moisture content by the meter sensor.

18. An apparatus for measuring the moisture content of stacked wood comprising:

an elongated probe supporting an electromagnetic wave responsive moisture sensor adjacent a first end portion;

a portable meter adapted to be electrically coupled to the probe sensor for displaying signals representing the moisture content of wood in proximity to the probe sensor, the meter being separable from the probe;

an electromagnetic wave responsive moisture sensor in the portable meter operable independently of the probe for measuring the moisture content of wood and for displaying signals representing the measured moisture content by the meter;

a connector on the portable meter for electrically coupling the meter to the probe sensor, the connector comprising means for disabling independent measurement of moisture content by the meter sensor;

a wood surface engaging element located on the first end portion and selectively movable from a first position toward a second position projecting outwardly from the probe a greater distance than when in the first position, whereby with the probe inserted between a first and a second layer of stacked wood, movement of the engaging element toward the second position pushes the forward end of the probe away from the first layer and towards the second layer;

a joint in the probe; and an articulated tip at the first end portion pivotable about the joint such that a bottom surface of the articulated tip can be laid flat against the second layer of stacked wood.

* * * * *